United States Patent [19]

Chambers et al.

[11] Patent Number: 4,476,329

[45] Date of Patent: Oct. 9, 1984

[54] SELECTIVE ALKYLATION OF PHENOL TO O-CRESOL

[75] Inventors: Gregory R. Chambers, Rexford; John J. Talley, Clifton Park, both of N.Y.

[73] Assignee: General Electric Company, Schenectady, N.Y.

[21] Appl. No.: 481,974

[22] Filed: Apr. 4, 1983

[51] Int. Cl.³ ............................................. C07C 37/16
[52] U.S. Cl. .................................. 568/804; 568/780; 568/794
[58] Field of Search ..................... 568/804, 794, 780

[56] References Cited

U.S. PATENT DOCUMENTS

| | | | |
|---|---|---|---|
| 3,417,149 | 12/1968 | Neuworth et al. | 568/804 |
| 3,479,410 | 11/1969 | Hamilton | 568/804 |
| 4,041,085 | 8/1977 | Frabetti, Jr. | 568/804 |
| 4,125,736 | 11/1978 | Leach | 568/804 |
| 4,400,557 | 8/1983 | Fremery et al. | 568/794 |
| 4,418,224 | 11/1983 | Bennett et al. | 568/804 |

Primary Examiner—Werren B. Lone
Attorney, Agent, or Firm—Richard J. Traverso; James C. Davis, Jr.; James Magee, Jr.

[57] ABSTRACT

A method is provided for producing o-cresol by simultaneously alkylating phenol with methanol and transalkylating 2,6-xylenol with phenol in the same reactor.

11 Claims, No Drawings

SELECTIVE ALKYLATION OF PHENOL TO O-CRESOL

This invention relates to a process for producing o-cresol. More particularly, this invention relates to a method of methylating phenol.

O-cresol, formula I below, is a starting material in the production of anti-oxidants.

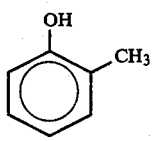
(I)

A method for producing o-cresol is disclosed in U.S. Pat. No. 3,446,856. The process disclosed involves selectively methylating the ortho position of phenol by reacting phenol with methanol in the presence of a magnesium oxide catalyst at a temperature in the range of 475°–600° C. Hamilton discloses that magnesium oxide is a unique catalyst for the reaction of methanol with phenols in that ortho alkylation occurs almost exclusively when the ortho position is unsubstituted. When utilizing unsubstituted phenol as the starting material, the principal products of the Hamilton process are o-cresol and 2,6-xylenol. Since 2,6-xylenol is the monomer used in the production of polyphenylene ether polymer, its production is often preferred. However, due to the independent market demand for o-cresol, it is desirable to produce o-cresol by a process which gives a high yield with little or no by-product, including 2,6-xylenol.

Where the selective production of o-cresol by methylation of phenol is desired, the reaction variables, such as temperature, flow rate, catalyst charge and phenol/methanol ratio, can be altered to favor production of o-cresol. However, under these conditions either the degree of phenol conversion is low, resulting in low yields of o-cresol, or there is a significant quantity of p-cresol contaminated 2,6-xylenol produced. The presence of p-cresol renders the 2,6-xylenol unsuitable for subsequent use.

The process comprising this invention overcomes the disadvantage of producing large quantities of 2,6-xylenol by-product and the disadvantage of producing p-cresol when methylating phenol to obtain high yields of o-cresol.

SUMMARY OF THE INVENTION

The present invention is based on the discovery that o-cresol can be produced with little or no 2,6-xylenol by-product from a reactor feed of 2,6-xylenol, phenol and methanol, by simultaneously transalkylating 2,6-xylenol and phenol while methylating phenol with methanol in the presence of a magnesium oxide catalyst in the same reactor under the same reaction conditions. These two reactions proceed simultaneously when the reactor feed in the vapor phase is passed over a magnesium oxide catalyst. Any magnesium oxide catalyst is suitable. Those which contain a manganese oxide promotor and an organic binder are preferred.

The alkylation reaction produced o-cresol and some by-products, including 2,6-xylenol and the transalkylation reaction consumes 2,6-xylenol by-product and added 2,6-xylenol to produce o-cresol. To obtain high yields of o-cresol with little or no by-product, the two reactions are controlled so that 2,6-xylenol consumption is at least equal to or exceeds 2,6-xylenol formation by the alkylation reaction. This balance is obtained by maintaining the reaction temperature within the range of about 400°–550° C., the molar ratio of phenol to methanol within the range of about 1:1 to 1:1.5 and the molar ratio of phenol to 2,6-xylenol within the range of about 1:1 to 1:0.25.

OBJECTS OF THE INVENTION

An object of the present invention is to produce o-cresol in high yields without producing 2,6-xylenol.

Another object of the present invention is to combine a transalkylation reaction and an alkylation reaction in one reactor to simultaneously produce o-cresol over the same catalyst and under the same reaction conditions.

Another object of the present invention is to utilize 2,6-xylenol that is contaminated with p-cresol.

Another object of the present invention is to produce high yields of o-cresol with little or no by-product.

DETAILED DESCRIPTION OF THE INVENTION

The process of this invention comprises passing phenol, methanol and 2,6-xylenol vapor through a reactor having a catalyst bed of magnesium oxide to produce o-cresol. To optimize the production of o-cresol and minimize by-product formation, such as 2,6-xylenol, the temperature of the catalyst bed is maintained within the range of about 400° C. to 550° C., the mole ratio of phenol to 2,6-xylenol in the feed is maintained within the range of about 1:1 to 1:0.25 and the mole ratio of phenol to methanol is maintained within the range of about 1:1 to 1:1.50. The phenol, methanol and 2,6-xylenol are passed through the reactor in vapor form. These reactants can be mixed to form a solution which is then vaporized or separate liquid streams of each reactant can be fed to one vaporizor, or the reactants may be vaporized separately and fed to the reactor as separate vapor feeds.

Where the reactor feed of phenol, methanol and 2,6-xylenol is passed over a magnesium oxide catalyst at a temperature over 400° C., the alkylation reaction and transalkylation reaction proceed simultaneously to produce o-cresol.

The alkylation reaction consumes phenol and methanol to produce a mixture of products comprising o-cresol, p-cresol, 2,6-xylenol, 2,4-xylenol and 2,4,6-trimethylphenol. The transalkylation reaction consumes 2,6-xylenol and phenol to produce a mixture of products comprising o-cresol, para-cresol, phenol, and 2,4,6-trimethylphenol. The net reaction which occurs within the reactor can be represented by the following equation:

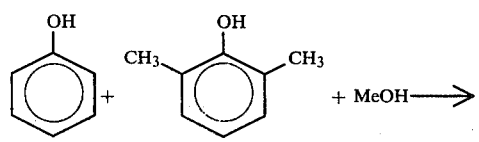

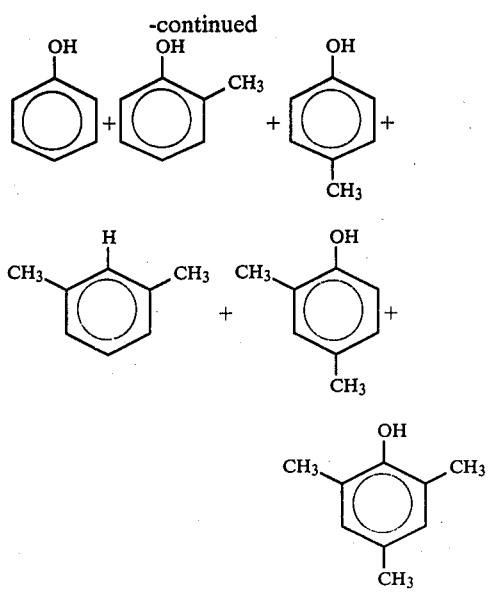

The transalkylation and the alkylation reaction compete under all reaction conditions, but the extent of competition is dependent on particular reaction conditions such as; for example, reaction temperature and the composition of reactor feed. To produce high yields of o-cresol with few by-products, the rates of both reactions are balanced by controlling the reaction temperature and the ratios of phenol to 2,6-xylenol and phenol to methanol in the reactor feed so that substantially all of the 2,6-xylenol formed in the alkylation reaction is converted to o-cresol by the transalkylation reaction.

A balance of 2,6-xylenol consumption and formation is approached where the reaction temperature is maintained within the range of about 400°–550° C. and the mole ratio of phenol to 2,6-xylenol in the reactor feed is within the range of about 1:1 to 1:0.25 and the mole ratio of phenol to methanol is in the range of about 1:1 to 1:1.5. When it is desirable to increase the consumption of 2,6-xylenol by this process, the transalkylation reaction rate can be increased without effecting the alkylation reaction significantly, by increasing the quantity of 2,6-xylenol within the reactor feed. The rate of the transalkylation reaction within the reactor can be increased to the extent that there is a net consumption of 2,6-xylenol by this process. This is obtained when the quantity of 2,6-xylenol utilized is sufficiently large to be a major component of the reactor feed; such as, where the mole ratio of phenol to 2,6-xylenol is about 1:1 and the mole ratio of phenol to methanol is about 1:1.

It is preferable to use a quantity of 2,6-xylenol which will limit the rate of transalkylation to proceed only to the extent necessary to consume a quantity of 2,6-xylenol equivalent to the quantity of 2,6-xylenol produced by the alkylation reaction. Maintaining this limit on the quantity of 2,6-xylenol in the reactor feed is preferred since the transalkylation reaction produces a significant quantity of by-products; such as p-cresol, 2,4-xylenol and 2,4,6-mesitol. In addition, the efficiency of this process is reduced where large quantities of 2,6-xylenol are utilized, since only a small percentage of the 2,6-xylenol which passes through the reactor undergoes transalkylation to form o-cresol. The preferred quantity of 2,6-xylenol within the reactor feed provides a mole ratio of phenol to 2,6-xylenol that falls within the range of about 1:0.5 to 1:0.25. At these quantities of 2,6-xylenol, the equilibrium between formation and consumption of 2,6-xylenol within the reactor is approached where the reaction temperature is within the range of about 400°–500° C. and the mole ratio of phenol to methanol is about 1:1.

It is preferred to maintain the mole ratio of phenol to methanol within the reaction feed at about 1:1. The use of large quantities of methanol within the reactor feed increases the quantity of phenol which is converted to o-cresol; but it also enhances the production of unwanted by-products, such as 2,6-xylenol.

As the temperature utilized in the reaction medium is increased from 400°–550° C., the rate of both the transalkylation reaction and the alkylation reaction increases, resulting in the production of a large quantity of o-cresol. However, the orthoselectivity of both reactions is reduced at higher temperatures, resulting in an increase in the formation of unwanted by-products such as 2,4-xylenol, 2,4,6-mesitol and p-cresol. In addition, the magnesium oxide catalyst exhibits a shorter lifetime at higher temperatures due to coking of the surface. The preferred reaction temperature is about 440° C. At this temperature, the ratio of o-cresol product to unwanted reaction products is high and coking of the magnesium oxide catalyst surface is not a problem.

Any catalytic form of magnesium oxide catalyst is suitable for use in this process. It is preferable that the magnesium oxide catalyst utilized be free of oxide compounds which tend to be acidic in nature; such as, aluminum oxide, silicon dioxide, silica-alumina, acidic clays, etc. However, small quantities of these materials can be tolerated if they are fired to a temperature where they have become inert. As such, they may be used as a support for the magnesium oxide without detrimental effect. Oxides of metals which are basic in nature, as is magnesium oxide, when present in minor proportions, have a promoting action which increases the activity of magnesium oxide, even though these compounds when used alone do not have the reactivity or selectivity in the alkylation reaction which magnesium oxide catalysts exhibit. Examples of such promotors include, manganese oxide, zinc oxide, lead oxide, etc. These promotors can be used as a heterogeneous mixture throughout the catalyst bed, coprecipitated with magnesium oxide or be utilized as a separate zone in the inlet of the reactor. If utilized, they are not present in excess of 10 weight percent of the total catalyst. Where manganese oxide is used, the preferred range is 2–5 weight percent of the total catalyst. These catalysts may have an inert organic or inorganic binder mixed within in order to permit them to be pelletized and easily handled in the process. Such binders may comprise up to 20 weight percent of the catalyst. Suitable organic binders include: polyphenylene oxide, graphite, etc. Silica is an example of a suitable inorganic binder. Polyphenylene oxide binders are preferred.

The activity of a given volume of magnesium oxide catalyst is dependent on the surface area of the catalyst exposed to the reactants. The more porous the catalyst, the more active. A suitably porous magnesium oxide catalytic material may be obtained by thermo-decomposition of magnesium carbonate, magnesium hydroxide, or basic magnesium carbonate. Basic magnesium carbonate being a complex of magnesium carbonate, magnesium hydroxide and water having the formula:

$$XMgCO_3 \cdot Mg(OH)_2 \cdot Y(H_2O),$$

where X and Y are from about 3 to about 5.

If desired, the magnesium compound can be coated on an inert carrier or binder, pelletized and then thermally decomposed to give a porous magnesium oxide coating on the inert substrate. The magnesium compound may be decomposed, i.e., calcined, prior to placement within the reactor or it may be generated from the precursor material within the reactor. It is preferable to calcine the material at about 300°–500° under an atmosphere such as hydrogen gas, nitrogen gas, helium gas, etc.

Magnesium oxide catalysts retain their activity for several days with little loss of specific activity. However, over long periods of operation, carbon deposition (coking) gradually decreases that activity. When this occurs, the catalyst can be regenerated by oxidation of the carbon by passing oxygen or air over the catalyst at temperatures in the range of about 400°–500° C.

A method utilized to retard the coking of the catalyst surface is to introduce steam into the reactor via the reactor feed so that the reaction takes place in the presence of steam. A suitable quantity of steam within the reactor is that obtained from a reactor feed having a concentration of 15–20 mass percent water. Where larger quantities of steam are present in the reactor, a decrease in o-cresol and 2,6-xylenol production is noticed due to side reactions caused by the steam. A convenient method for introducing steam to the reactor is to utilize an aqueous/phenol solution in the reactor feed to supply vaporous phenol and steam to the reactor.

Both products and unreacted starting materials exit the catalyst bed of the reactor in vapor form and thereafter condense to a liquid. This can be accomplished by any conventional means, such as a common air or water condenser. The products are then separated from the condensed reactor effluent, preferably by distillation in a conventional distillation apparatus. The first distillation fractions contain water unreacted phenol and methanol, which are suitable for recycling to the reactor. Substantially pure o-cresol product comprises the following distillation fraction and the next distillation fraction consists of 2,6-xylenol, a portion thereof being formed in the reactor and another portion having passed through the reactor uneffected. This distillation fraction may contain trace amounts of p-cresol produced in the reactor or placed within the reactor feed. This distillation fraction is suitable for recycling to the reactor. P-cresol does not interfere with the alkylation-transalkylation reactions within this process and its presence in small quantities among the starting materials does not have a detrimental effect on the results obtained. Any p-cresol that is present among the starting materials either passes through the reactor uneffected or is further alkylated to 2,4-xylenol, 2,4,6-mesitol, etc. When p-cresol becomes further alkylated, the products obtained have high boiling points and remain at the bottom of the distillation pot during removal of the distillation fractions.

Both reactions proceed smoothly at atmospheric pressure which makes it convenient to carry out the process, since it eliminates the need for complex equipment and eliminates the hazards that are characteristic to reactions which proceed under pressure. However, pressures above and below atmospheric pressure can be used when desired.

The flow rate of reactants is not critical to obtain a balance of consumption and formation of 2,6-xylenol within the reactor. Flow rate does effect the product yield by determining the amount of contact time between the reactants and the catalyst. Due to the differences in the specific activities of magnesium oxide catalysts, each particular catalyst will have a different optimum flow rate than another. The more active the catalyst, the shorter the contact time necessary to produce the same quantity of product. Therefore, to obtain a particular quantity of product, higher space velocities can be used with more active catalysts, while lower space velocities are necessary with less active catalysts. A flow rate which is too high will flood the catalyst and not permit the reaction to proceed. Flow rates which are too low will reduce the ortho selectivity of the magnesium oxide resulting in large quantities of by-products. Where the catalyst utilized contains manganese oxide promoter within the range of 2–5 weight percent and an organic binder within the range of 0–10 weight percent, a flow rate having a liquid hourly space velocity in the range of about 0.5 to 3 is suitable. The preferred flow rate has a 0.5 liquid hourly space velocity.

To minimize the decomposition of the reactants during vaporization, the vaporizers should be maintained at the minimum temperature necessary to vaporize the reactants. The vapors are then pre-heated to the temperature of the reactor so as not to cool the catalyst below the reaction temperature selected. This can be accomplished by passing the vaporized reactants through a heated tube of metal or glass or by passing the vaporized reactants over heated glass beads just prior to entry into the catalyst bed. It is preferable to utilize the same heating medium to pre-heat the vapors that is used to heat the catalyst bed so as to maintain a stable reaction temperature within the reactor.

The process can be carried out in a conventional reactor used for vapor phase reactions over a solid catalyst. For example, a tubular reactor of glass or metal filled with a static bed of magnesium oxide catalyst is suitable. The reactor is heated to the desired temperature by any conventional means; for example, it can be heated by surrounding the reactor with an electric heater or by surrounding the reactor with a heated gas or liquid. Multiple electric heaters with separate controls permit the catalyst bed temperature to be controlled quite easily, even though the reaction is exothermic. Such an apparatus is capable of maintaining the catalyst bed temperature within 10 degrees of the temperature selected.

In order that those skilled in the art may better understand this invention, the following experiments are provided by way of illustration and not by way of limitation.

EXPERIMENTAL PROCEDURES

In each of the experiments which illustrate this invention the following procedure was utilized.

An 18 inch×1 inch I.D. hot tube reactor was prepared by wrapping heat tape to three equally spaced zones and insulating with glass wool. Three thermocouples were installed in the vigreaux points at 6 inch intervals along the length of the tube. The temperature in each zone was maintained within 10° of the reaction temperature selected. The reactor was packed with 5 milliliter glass beads followed by 100 ml. of magnesium oxide catalyst having 2–5 weight percent manganese oxide promoter and 1–20 weight percent polyphenylene oxide binder. The last three to four inches of the reactor were packed with glass beads. The catalyst was calcined at 500° C. for four hours under a flow of hydrogen gas (0.1 scfh). The catalyst bed was then brought to the desired temperature. The reactants were introduced at the top of the bed with a pump at a flow rate having a 0.5 liquid hourly space velocity. A liquid phenol solution of 11 weight percent water was employed to provide steam within the reactor. Products which exited the reactor were condensed and analyzed by gas chromatography. Twenty seven experiments were run with varying reactor feed concentrations and reaction temperatures. The results of these experiments appear in Table I.

TABLE I

| Expt # | Temp (°C.) | Feed (Molar Ratio) | | | Feed Mass % | Product Composition (Mass %) | | | | | |
|---|---|---|---|---|---|---|---|---|---|---|---|
| | | Phenol | Methanol | 2,6-xylenol | 2,6-xylenol | Phenol | o-cresol | p-cresol | 2,6-xylenol | 2,4-xylenol | 2,4,6-mesitol |
| 1 | 400 | 1.0 | 1.5 | 1.0 | 56.1 | 28.4 | 15.6 | .8 | 53.6 | 1.9 | 0.7 |
| 2 | 450 | 1.0 | 1.5 | 1.0 | 56.1 | 9.0 | 26.8 | .3 | 54.7 | 3.6 | 5.2 |
| 3 | 500 | 1.0 | 1.5 | 1.0 | 56.1 | 9.5 | 34.0 | 1.5 | 45.1 | 4.9 | 3.8 |
| 4 | 400 | 1.0 | 1.5 | .5 | 39.5 | 38.7 | 20.6 | .5 | 39.9 | .5 | .2 |
| 5 | 450 | 1.0 | 1.5 | .5 | 39.5 | 12.6 | 33.7 | .0 | 49.7 | 1.7 | 1.8 |
| 6 | 500 | 1.0 | 1.5 | .5 | 39.5 | 10.5 | 37.5 | .0 | 47.9 | 2.1 | 1.7 |
| 7 | 400 | 1.0 | 1.0 | .5 | 38.0 | 49.1 | 12.2 | .7 | 37.4 | .3 | .0 |
| 8 | 450 | 1.0 | 1.0 | .5 | 38.0 | 23.4 | 33.5 | .7 | 40.2 | 1.5 | .5 |
| 9 | 500 | 1.0 | 1.0 | .5 | 38.0 | 20.9 | 38.9 | .0 | 37.2 | 1.9 | .6 |
| 10 | 400 | 1.0 | 1.0 | .25 | 24.4 | 61.3 | 13.7 | .4 | 24.3 | .2 | .0 |
| 11 | 450 | 1.0 | 1.0 | .25 | 24.4 | 34.1 | 35.9 | .0 | 28.0 | 1.3 | .4 |
| 12 | 500 | 1.0 | 1.0 | .25 | 24.4 | 27.7 | 42.5 | .0 | 27.5 | 1.6 | .5 |
| 13 | 400 | 1.0 | 1.0 | .33 | 30.1 | 57.5 | 11.8 | .4 | 29.7 | .2 | .0 |
| 14 | 450 | 1.0 | 1.0 | .33 | 30.1 | 35.1 | 30.9 | .5 | 31.5 | .8 | .2 |
| 15 | 500 | 1.0 | 1.0 | .33 | 30.1 | 26.4 | 39.7 | .0 | 32.3 | 1.2 | .4 |
| 16 × 10H$_2$O | 450 | 1.0 | 1.0 | .33 | 29.9 | 40.9 | 26.9 | .6 | 30.5 | .8 | .2 |
| 17 × 10H$_2$O | 500 | 1.0 | 1.0 | .33 | 29.9 | 30.5 | 37.5 | 1.0 | 29.0 | 1.5 | .5 |
| 18 | 400 | 1.0 | 1.0 | 0.0 | 0.0 | 91.5 | 8.4 | .1 | .2 | .0 | .0 |
| 19 | 425 | 1.0 | 1.0 | 0.0 | 0.0 | 82.2 | 16.7 | .2 | .8 | .1 | .0 |
| 20 | 450 | 1.0 | 1.0 | 0.0 | 0.0 | 65.4 | 31.4 | .0 | 2.8 | .3 | .0 |
| 21 | 475 | 1.0 | 1.0 | 0.0 | 0.0 | 51.6 | 41.5 | .0 | 5.9 | .7 | .1 |
| 22 | 500 | 1.0 | 1.0 | 0.0 | 0.0 | 42.5 | 47.7 | .0 | 8.3 | .9 | .2 |
| 23 | 400 | 1.0 | 0.0 | .5 | 39.5 | 59.1 | 1.7 | .5 | 38.6 | .0 | .0 |
| 24 | 425 | 1.0 | 0.0 | .5 | 39.5 | 57.9 | 4.3 | .7 | 36.9 | .0 | .1 |
| 25 | 450 | 1.0 | 0.0 | .5 | 39.5 | 55.7 | 9.3 | .9 | 33.8 | .0 | .2 |
| 26 | 475 | 1.0 | 0.0 | .5 | 39.5 | 54.2 | 13.1 | 1.0 | 31.3 | .0 | .3 |
| 27 | 500 | 1.0 | 0.0 | .5 | 39.5 | 53.7 | 15.2 | 1.0 | 30.0 | .0 | .3 |

Experiments 1–3 illustrate the effect of using excess methanol and 2,6-xylenol in the reactor feed. Large quantities of phenol are converted to o-cresol but large quantities of 2,4-xylenol, 2,4,6-mesitol and p-cresol are produced. Consumption of 2,6-xylenol is also noticed.

In experiments 4–6 excess methanol is present in the reactor feed. High phenol conversion to o-cresol results with large quantities of by-product produced, including 2,6-xylenol.

Experiments 7–15 were run with reactor feed compositions within the preferred range of this invention. Small quantities of by-product are produced with large quantities of o-cresol. Production of 2,6-xylenol is negligible.

Experiments 16 and 17 show the detrimental effect of large quantities of steam present in the reactor. The reactor had 10 times the quantity of water present in the standard experimental procedure described above. A decrease in phenol conversion is shown and an increase in by-product production results.

Experiments 18–22 provide a comparison of results obtained where the transalkylation is maintained at a minimum. No 2,6-xylenol was present in the reactor feeds of these experiments. Large quantities of by-product were obtained in these experiments, particularly 2,6-xylenol.

Experiments 23–27 demonstrate the effects of running the transalkylation reaction independent of the alkylation reaction. No methanol was introduced in the reactor feed of these experiments. The results show low phenol conversion to o-cresol and a significant quantity of by-products.

Although the above experiments have shown various modifications of the present invention, further modifications are possible in light of the above teachings by one skilled in the art without departing from the spirit and scope of this invention.

What is claimed is:

1. A process for producing o-cresol which comprises reacting in vapor phase, phenol, methanol and 2,6-xylenol on a magnesium oxide catalyst at a temperature between about 400° C.–550° C. to simultaneously methylate phenol with methanol and transmethylate 2,6-xylenol with phenol.

2. A process as in claim 1 wherein the mole ratio of phenol to methanol is between about 1:1 to 1:1.5 and the mole ratio of phenol to 2,6-xylenol is between about 1:1 to 1:0.25.

3. A process as in claim 1 wherein the catalyst is the calcination residue of precursor material selected from the group consisting of: magnesium carbonate, magnesium hydroxide, basic magnesium carbonate, magnesium carbonate containing about 0–5 weight percent manganese oxide and magnesium hydroxide containing about 0–5 weight percent manganese oxide.

4. A process as in claim 1 wherein the catalyst is magnesium oxide containing about 2–5 weight percent manganese oxide and about 1 to 10 weight percent organic binder.

5. A process as in claim 1 wherein the mole ratio of phenol to methanol is about 1:1 and the mole ratio of phenol to 2,6-xylenol is between about 1:0.5 to 1:0.25.

6. A process as in claim 5 wherein the reaction is maintained at a temperature of about 440° C.

7. A process as in claim 6 wherein the catalyst is magnesium oxide containing about 2–5 weight percent manganese oxide and about 1–10 weight percent polyphenylene oxide.

8. A process according to claim 1 wherein the reaction is carried out in the presence of steam.

9. A process as in claim 8 wherein the mole ratio of phenol to steam is between about 1:0.33 to 1:0.6.

10. A process for producing o-cresol from phenol, methanol and 2,6-xylenol which comprises reacting in vapor phase, phenol, methanol and 2,6-xylenol over a magnesium oxide catalyst in the presence of steam at a temperature of about 440° C. to simultaneously methylate phenol with methanol and transmethylate 2,6-xylenol with phenol, said magnesium oxide catalyst comprising magnesium oxide, about 2–5 weight percent manganese oxide and about 1–10 weight percent polyphenylene oxide, the mole ratio of phenol/methanol being equal to about 1:1, the mole ratio of phenol/2,6-xylenol being equal to about 1:0.33, and the mole ratio of phenol/steam being equal to about 1:0.6.

11. A process for producing o-cresol from methanol, phenol and 2,6-xylenol which comprises reacting in vapor phase, methanol and 2,6-xylenol over a magnesium oxide catalyst in the presence of steam at a temperature of about 440° C. to simultaneously methylate phenol with methanol and transmethylate 2,6-xylenol with phenol, said catalyst comprising magnesium oxide, about 2–5 weight percent manganese oxide and about 1–10 weight percent polyphenylene oxide, the mole ratio of phenol/methanol being equal to about 1:1, the mole ratio of phenol/2,6-xylenol being equal to about 1:0.05, and the mole ratio of phenol/steam being equal to about 1:0.6.

* * * * *